United States Patent [19]

Wuertele

[11] 4,280,124

[45] Jul. 21, 1981

[54] CORROSION DETECTOR

[76] Inventor: James W. Wuertele, 155 Acalanes Dr., Apt. 27, Sunnyvale, Calif. 94086

[21] Appl. No.: 950,663

[22] Filed: Oct. 12, 1978

[51] Int. Cl.$^3$ ............................................. G08B 21/00
[52] U.S. Cl. ..................................... 340/650; 307/95; 324/127
[58] Field of Search .................. 340/650, 651; 307/95, 307/327, 416; 324/51, 65 CR, 127, 102; 204/196, 147

[56] References Cited

U.S. PATENT DOCUMENTS

| | | | |
|---|---|---|---|
| 2,839,722 | 6/1958 | Marsh | 324/65 CR |
| 2,869,003 | 1/1959 | Marsh et al. | 307/95 |
| 3,102,979 | 9/1963 | Schaschl | 307/95 |
| 3,411,087 | 11/1968 | Vogel et al. | 324/127 |
| 3,769,521 | 10/1973 | Caldwell et al. | 307/95 |
| 3,769,926 | 11/1973 | Race | 307/95 |
| 3,857,096 | 12/1974 | Gregory | 324/127 |
| 3,947,759 | 3/1976 | Briggs | 340/650 |
| 3,986,116 | 10/1976 | Smith et al. | 324/127 |
| 4,110,683 | 8/1978 | Cason et al. | 340/650 |
| 4,117,345 | 9/1978 | Balcom | 307/95 |
| 4,134,059 | 1/1979 | Stankoff | 324/127 |

OTHER PUBLICATIONS

Brochures Prepared by Applicant for the California Assoc. of Harbormasters and Port Captains, Inc., Oct. 28, 1976 and Oct. 13, 1977.
Brochures Prepared by Applicant for the Pacific Coast Congress of Harbormasters and Port Managers, Inc., Apr. 15, 1977.
Commercial Ad from McMillen Marine, Inc. for "Electronic Corrosion Control", 12/1/74.
Commercial Ad from General Electric for "Ground Break System", 8-2-76.

Primary Examiner—Gerald L. Brigance
Attorney, Agent, or Firm—Flehr, Hohbach, Test

[57] ABSTRACT

A corrosion detector for use in detecting corrosion currents in the form of AC and DC leakage currents which occur in a marina. The detector monitors AC power and ground lines or other conductive lines interconnected between boats in a marina and includes a transducer to detect leakage currents which occur in the boats connected to the power lines. The detector provides either an alarm signal or displays the damage rate and location to indicate corrosion currents in one or more of the boats in a harbor.

10 Claims, 10 Drawing Figures

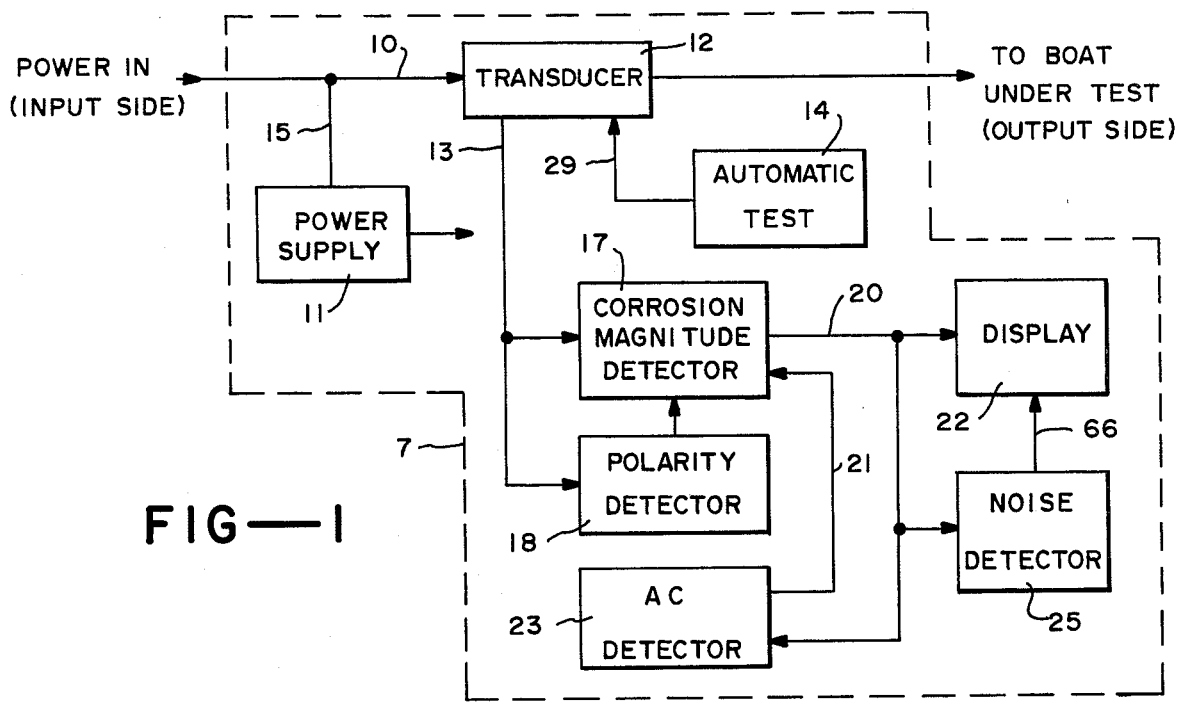
FIG—1
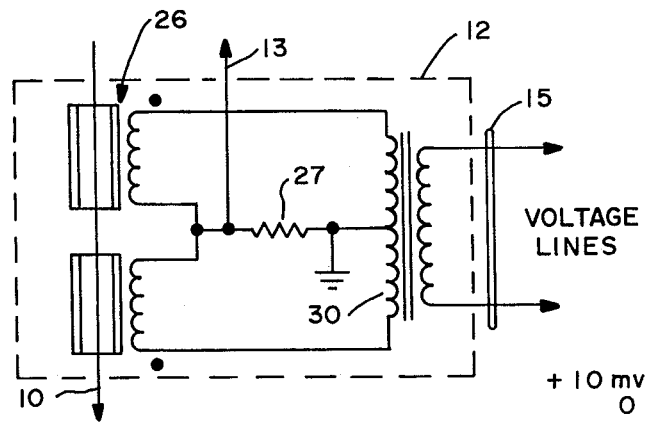
FIG.—2
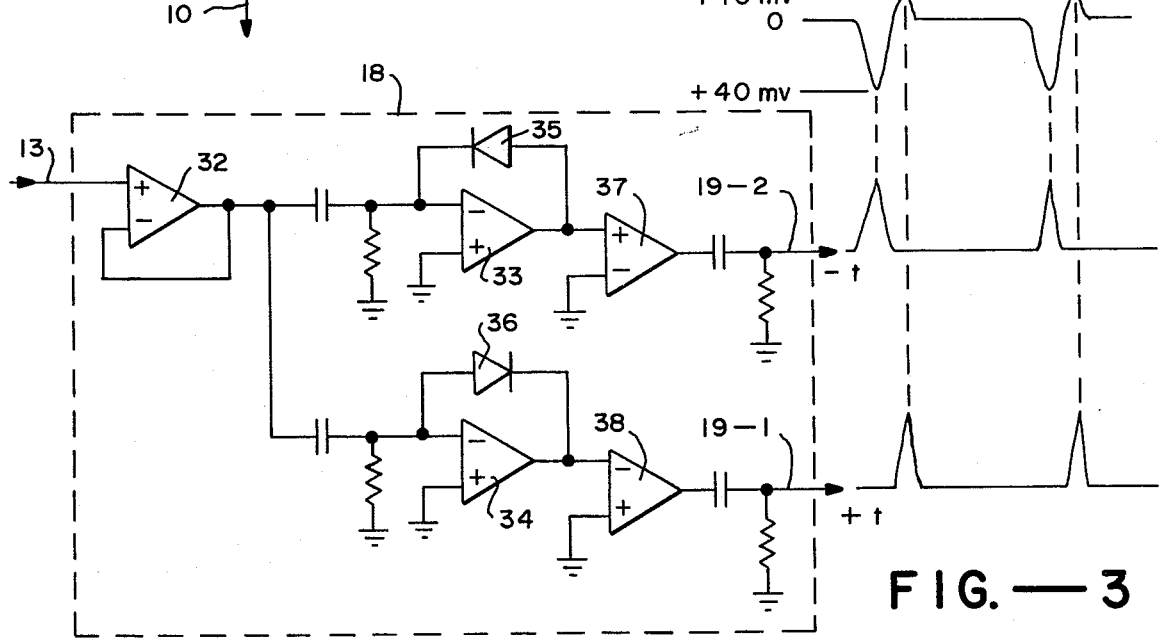
FIG.—3

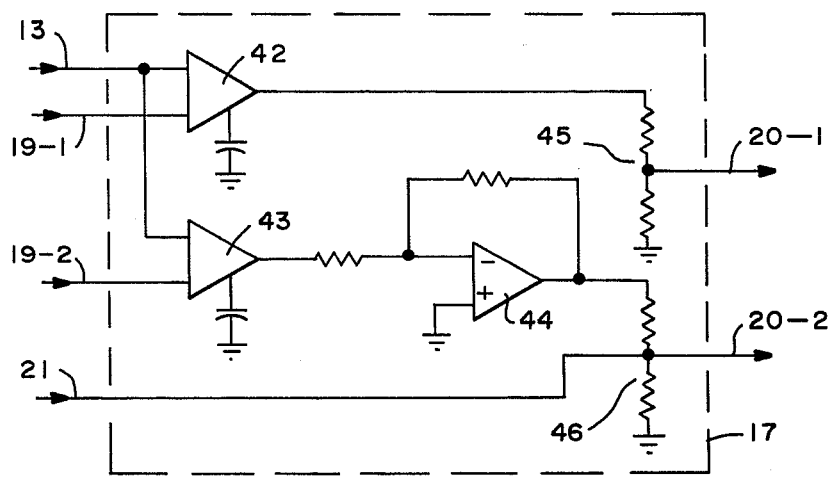
FIG.—4
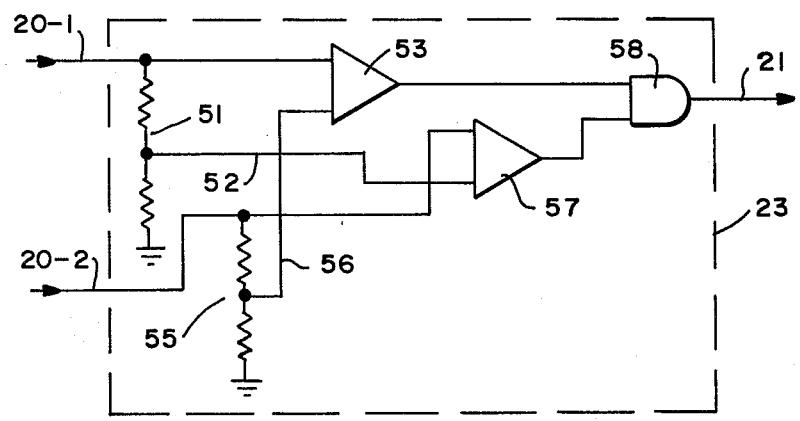
FIG.—5
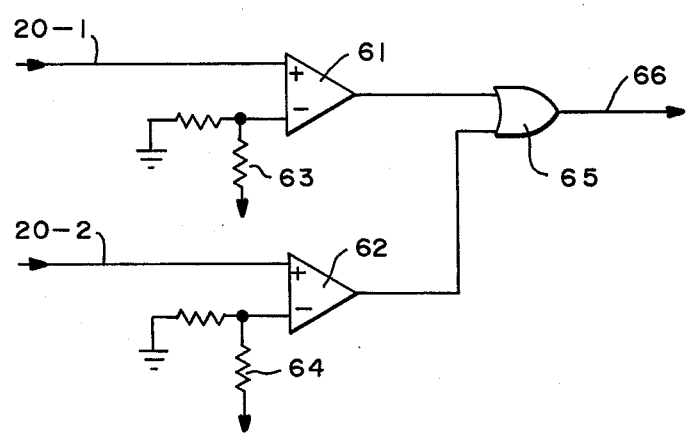
FIG.—6
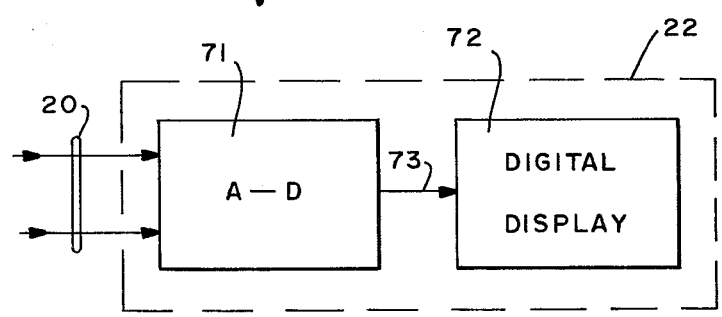
FIG.—7

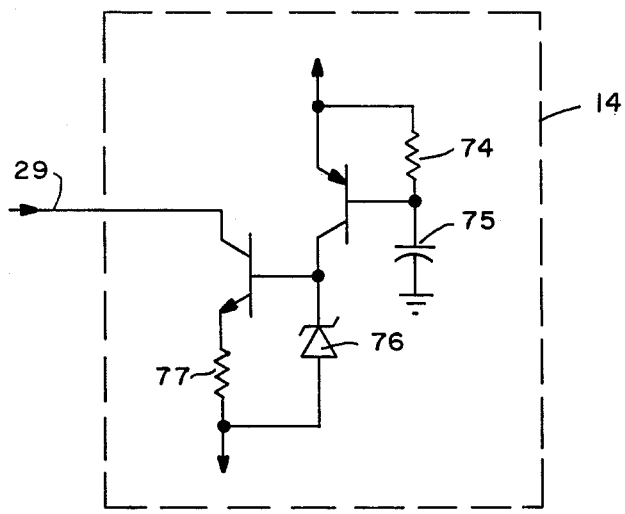
FIG.—8
A ——————————— $I_c = 0$
B ⌒⌒⌒ $I_c = -DC$
C ⌢⌢⌢ $I_c = +DC$
D ∼∼∼ $I_c = AC$
FIG.—9
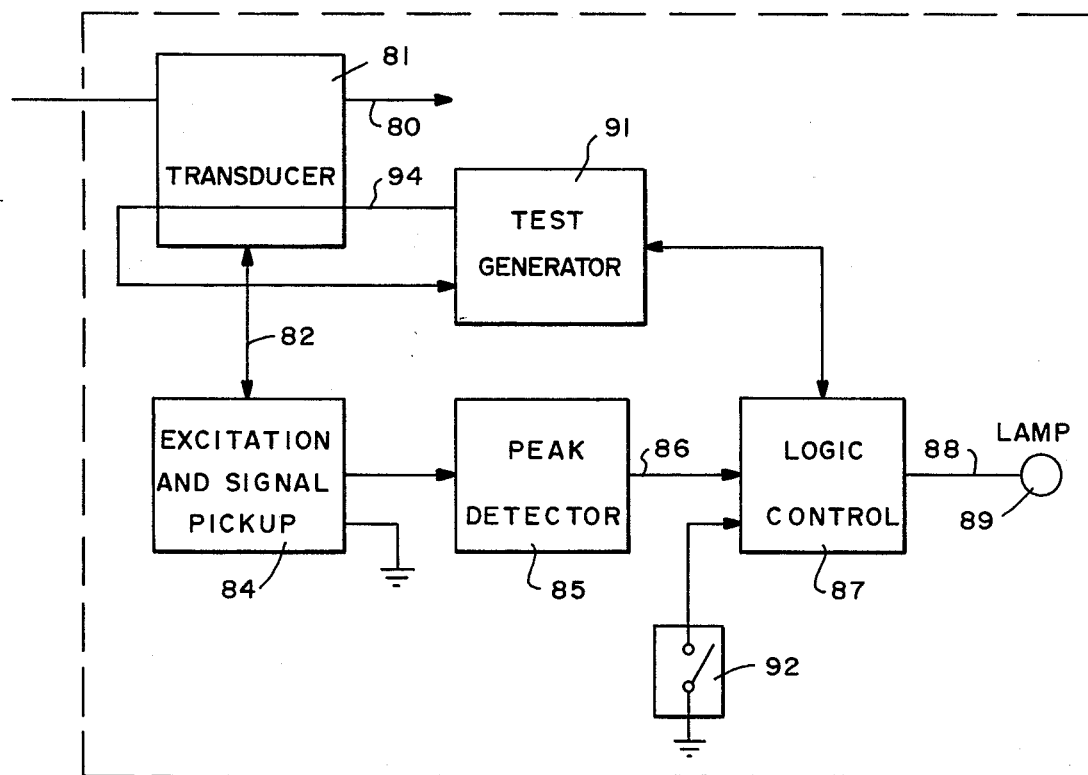
FIG.—10

CORROSION DETECTOR

BACKGROUND OF THE INVENTION

The present invention relates to a corrosion detector for use such as in a marina environment.

Corrosion damage to the hulls and engine components of boats in a harbor can be caused during the electrical interconnection of a group of boats to a dock's AC distribution power system at a modern marina. Electrical currents caused by the appearance of a leakage of DC or AC voltage from the intended conductors can be conducted between the boats in a harbor since the water can become an electrical conductor.

The occurrence of a leakage current between boats interconnected in a harbor or between a boat and the dock can cause damage to some or all of the boats in the harbor as a result of dissolving of the hull by the electrical current. The extent of damage depends upon the amount of metal dissolved. It is known as a result of experiments by Faraday that one ampere of direct current in a conductive medium such as ocean water can dissolve about one gram of metal such as iron in one hour. Continuous corrosion currents in a marina environment can cause serious damage to boats and/or their components.

Corrosion currents which can cause the corrosion damage are DC leakage currents, AC leakage currents, and galvanic currents.

DC leakage corrosion can occur between vessels interconnected electrically between each other and a harbor dock by the harbor wiring. AC leakage current usually comes from a 60 hertz line voltage distributed to connected vessels and cause damage at a lower rate for the same power due to a saturation effect caused by the ions being unable to follow polarity refersals.

Galvanic current can occur between one vessel and nearby vessels similarly connected when the subject vessel has lost all its zinc electrodes. At that time, it begins to draw on zincs (galvanic current) of nearby vessels for galvanic protection. These zincs then dissolve even faster and an avalanche effect occurs that will affect more and more boats over an ever-widening area of the harbor. The rate of damage is much less than that usually due to electrical leakage but it occurs more often.

Although prior art equipment has been developed to provide continuous biasing of hulls which may react to currents of the DC and galvanic type, no equipment has been designed to detect corrosive current interactions between boats and the harbor safety ground electrodes for use to analyze rate of damage and source of the currents. One example of the prior art is an impressed current system, which provides biasing of a hull of a single boat against a submerged electrode, isolated from affecting other boats.

However, a problem occurring with impressed current systems is that they are used to protect against galvanic corrosion in one boat and thus will not respond to leakage currents in the rest of the harbor.

There are various devices designed to detect leakage AC currents in an AC power wiring and load system but are constrained to sense leakage in consumer or industrial applications such as personal safety and AC equipment leakage to the grounding conductor. In either case either the conductors or the grounding current is monitored and the function of the response is to stop the power flowing to the fault. There has generally not been the equipment available that can detect DC as well as AC leakage current occurring in a marina environment.

In view of the above background, it is an objective of the present invention to provide a corrosion detector for use in a marina environment to detect corrosion currents that could cause damage to the hull and equipment of the boats in the harbor.

SUMMARY OF THE INVENTION

The present invention relates to a corrosion detector for use in a marina. In one embodiment, the detector includes a transducer provided to sense corrosion currents which can occur, for example, in an AC power line which is providing necessary power to one or more boats in a harbor. If the corrosion current is a DC leakage current, the detector includes means for generating a control signal representing the polarity of the DC leakage current. If the corrosion current is an AC leakage current, the detector includes means for generating a control signal representing the presence of the AC corrosion current.

The detector also includes means for generating a signal representing the magnitude of the corrosion current and display means for displaying a relation to the magnitude of the corrosion current, whether is is AC or DC corrosion, and the polarity and thereby the location of the DC corrosion current damage.

In another embodiment, the detector includes transducer means for detecting the occurrence of a corrosion current such as an AC or DC leakage current in an AC power line which is providing power to all of the boats in a marina environment. The detector generates a control signal representing a corrosion current and alarm means responsive to the control signal generated by the transducer means are provided to present a visual or audio alarm signal representing the occurrence of a corrosion current in one of the boats.

In accordance with the above summary, the present invention achieves the objective of providing a corrosion detector for detecting corrosion currents such as DC and AC leakage currents which can occur in a power distribution line in a marina environment.

Other objects and features of the invention will become apparent from the following description when taken in conjunction with the drawings.

DESCRIPTION OF THE DRAWINGS

FIG. 1 depicts a block diagram of one embodiment of a corrosion detector according to the present invention.

FIG. 2 depicts a schematic representation of a transducer, which forms a portion of FIG. 1.

FIG. 3 depicts a schematic representation of a polarity detector, which forms a portion of FIG. 1.

FIG. 4 depicts a schematic representation of a corrosion magnitude detector, which forms a portion of FIG. 1.

FIG. 5 depicts a schematic representation of an AC current detector, which forms a portion of FIG. 1.

FIG. 6 depicts a schematic representation of a noise detector circuit, which forms a portion of FIG. 1.

FIG. 7 depicts a block diagram of a display circuit, which forms a portion of FIG. 1.

FIG. 8 depicts a schematic representation of a test circuit, which forms a portion of FIG. 1.

FIG. 9 depicts a timing diagram illustrating various corrosion currents.

FIG. 10 depicts a block diagram of another embodiment of a corrosion detector according to the present invention.

DETAILED DESCRIPTION OF THE INVENTION

FIG. 1 depicts a block diagram of a corrosion detector 7 according to the present invention, in which detector 7 is connected to an AC power line 10 which provides power in a harbor to one or more boats. Detector 7 senses corrosion currents which can occur in power line 10 (power and safety ground conductors) by means of transducer 12, which is a magnetic detector which can monitor the instantaneous magnitude of electrical currents in an otherwise benign media such as an AC power line, telephone line or water, which are conductive media, to complete an electrical path between the source of a corrosion current and a dissipating conductive medium.

Detector 7 provides detection of DC leakage, AC leakage, and galvanic corrosion currents in AC power lines or other conductors which can cause electrolytic corrosion damage in marina and other environments. Such damage can be in the form of corrosion to portions of the hull or engine of a boat.

Transducer 12 in FIG. 1 can detect leakage currents between boats in a harbor by intercepting them in a benign conductive medium without affecting the conduction of the current. Transducer 12 will generate control signals on bus 13 which represent the occurrence on bus 10 of corrosion currents such as DC or AC leakage currents.

Corrosion magnitude detector 17 and polarity detector 18 are connected to receive the control signals on bus 13 and as will be described in more detail are responsive to the signals on bus 13 thereby generating control signals on buses 19, 20 which represent, respectively, an indication of the polarity and magnitude of the corrosion currents.

Display 22 is connected to receive the control signals on bus 20 for displaying the magnitude of the corrosion current, if desired, and can display whether the corrosion current detected is a DC or AC leakage current and, if a DC leakage current, the polarity of that current. The polarity of the leakage current is important since detector 7 of FIG. 1 can give an indication whether the boat or the harbor is the location of the damage due to corrosion currents by proper connection of detector 7 to power line 10. The magnitude displayed in a digital high-resolution form will determine the source boat as its reading will be the sum of the readings of the rest.

AC detector circuit 23 is responsive to the magnitude and polarity signal on bus 20 and generates on bus 21 a control signal representing the occurrence of an AC leakage current, as will be described in conjunction with FIG. 5.

In FIG. 1, test circuit 14 is connected to transducer 12 via bus 29 and generates a test signal on bus 29 to simulate a corrosion current, which when detected by transducer 12 provides self testing capabilities. The noise detector circuit 25 will be described in conjunction with FIG. 6.

Referring now to FIG. 2, the transducer 12 of FIG. 1 is schematically depicted and shows the transformer winding cores 26 arranged in a opposite sense in order to detect the corrosion currents on power line 10. The corrosion currents, such as AC and DC leakage currents, which can occur are depicted in FIG. 9. In FIG. 2, the transformer windings 26 of transducer 12 provide a benign non-conductive sensing medium for any corrosion currents which occur on the conductors of bus 10.

Transducer 12 senses a corrosion voltage signal across resistor 27 and thereby provides a control signal on bus 13 representing the occurrence of a corrosion current. Transformer 30 provides necessary voltage to transducer 12 as excitation. The imbalance of the inductive reaction of the cores 26 caused by corrosion currents on bus 10 provide the corrosion control signal on resistor 27 and bus 13. Both the transformer 30 and the power supply are fed line voltage by conductive means.

Referring now to FIG. 9, the corrosion currents which occur and can be detected are illustrated. In FIGS. 9B-9D, the positive DC, negative DC and AC signals due to corrosion currents are illustrated. The positive and negative DC corrosion currents are identical except for the polarity of the signals. If the connections of detector 7 of FIG. 2 were reversed, the detector circuit would display a change in the polarity of DC leakage current. This provides the capability to identify a particular boat in a harbor which is receiving corrosion currents.

In FIG. 3, the polarity detector 18 provides trigger signals on buses 19-1 and 19-2 indicating when the peak value of a corrosion current signal occurs. In FIG. 3, a negative DC leakage current is depicted with the magnitude of the negative peak signal approximately −40 millivolts and the magnitude of the corresponding positive peak signal approximately +10 millivolts. The corrosion current signal such as depicted in FIG. 3 and detected by transducer 12 of FIG. 2, is coupled on bus 13 into polarity detector circuit 18 through typical buffer 32 into conventional operation amplifiers (such as 358) 33, 34 respectively. Diodes 35, 36 are oppositely connected to amplifiers 33, 34 respectively, thereby generating trigger control signals on buses 19-1 and 19-2 through conventional amplifiers 37, 38. It can be seen in FIG. 3 that the trigger signal on bus 19-2 occurs when the negative peak signal occurs from the negative DC leakage current and similarly the position trigger signal on bus 19-1 occurs when the positive peak pulse occurs on the negative DC leakage current. Polarity detector circuit 18 in FIG. 3 thereby provides on buses 19-1, 19-2 trigger control signals representing respectively the occurrence of the positive and negative peaks of a control signal caused by DC leakage current.

Referring now to FIG. 4, the trigger signals on buses 19-1 and 19-2 are connected to corrosion magnitude detector circuit 17 together with the corrosion control signals on bus 13. In FIG. 4, the control signals are coupled into conventional sample and hold circuits (typically LF 398) 42, 43. Circuit 42 generates on bus 20-1 through a voltage divider circuit 45 a control signal representing the magnitude of the positive peak of the leakage current.

Similarly, circuit 43 receives the corrosion current signal on bus 13 and the negative trigger on bus 19-2 which when inverted through conventional amplifier 44 and passed through conventional voltage divider circuit 46 generates on bus 20-2 the absolute magnitude of the negative peak value of the corrosion current detected.

Magnitude detector circuit 17 also receives on bus 21 an AC indication signal which will be described in more detail in conjunction with FIG. 5.

Assuming a DC corrosion current has been detected by transducer 12 of FIG. 2, the magnitude and polarity control signals on buses 21, 20-2 of FIG. 4 are coupled into the display circuit 22 of FIG. 7, which includes a conventional analog to digital converter (such as 7106) 71, for receiving the differential input signals on buses 20-1, 20-2 which represent the difference between the peak values of the corrosion current detected. Circuit 71 provides to digital display circuit 72 via appropriate logic circuitry (not shown) on bus 73 the polarity and magnitude of the corrosion current detected. Display circuit 72 can display the magnitude and polarity of the corrosion current detected or alternatively could display the magnitude of resultant corrosion from the detected corrosion current in terms of grams of iron dissolved per hour.

Referring now to FIG. 5, a schematic representation of the AC detector circuit 23 of FIG. 1 is depicted with the peak value signals on buses 20-1 and 20-2. The peak signal on bus 20-1 is connected to comparator 53 and connected through voltage divider 51 and bus 52 to comparator 57. Similarly, the absolute value of the negative peak signal on bus 20-2 is connected directly to comparator 57 and through voltage divider circuit 55 and bus 56 to comparator 53.

An AC corrosion current such as depicted in FIG. 9 is symmetrical while the DC leakage currents are asymmetrical with respect to the time axis. Voltage divider circuits 51, 55 provide on buses 52, 56 reduced values of the peak current signals on buses 20-1, 20-2. In one embodiment, the relative magnitudes of the signals developed on buses 52, 56 are approximately 80% of the peak values. If an AC current signal is being detected, the outputs of comparators 53, 57 will both be high and hence the AND gate 58 will be high representing a control signal on bus 21 indicating the presence of an AC corrosion current. This AC indication signal on bus 21 is connected to detector circuit 17 in FIG. 4 which when connected to display circuit 22 through appropriate logic circuitry will provide an indication on display 72 that an AC corrosion current is detected.

In FIG. 5, if DC corrosion currents are being detected, the outputs of comparators 53, 57 will be opposite in sense and hence the output of AND gate 58 will be low thereby indicating the presence of a DC corrosion current.

Referring now to FIG. 6, a zero signal decision or noise circuit 25 is illustrated which can be incorporated into the present invention. The need for a zero signal decision is desirable to suppress premature corrosion location (polarity) indications in the event that noise level signals are being indicated rather than corrosion currents. In FIG. 6, the peak values on buses 20-1, 20-2 are connected to conventional comparators 61, 62. If the corrosion current signals on either of buses 20-1, 20-2 are larger than a predetermined threshold established by the voltage dividers 63, 64 comparators 61, 62 enable OR gate 65 to generate a non-zero signal, which indicates that corrosion current is in fact being detected and is not a signal due to noise occurring in the system.

Referring now to FIG. 8, the self test circuit 14 of FIG. 1 is schematically represented in which a self-induced current on bus 29 is connected to transducer 12 of FIG. 1. The purpose of test circuit is to provide automatic self testing capabilities for the corrosion detector of FIG. 1. The corrosion current indicator signal on bus 29 can be generated by the circuitry of FIG. 8 and the duration of the signal is controlled by the time constant developed by resistor 74 and capacitor 75, thereby generating a pulse or corrosion current indicator signal on bus 29 of predetermined duration, which when sensed by transducer 12 in FIG. 1 will generate a control signal on bus 13. The magnitude of the corrosion current on bus 29 is determined approximately by the voltage across diode 76 divided by the value of resistor 77.

Referring now to FIG. 10, another embodiment according to the present invention is illustrated in block diagram form, in which a transducer 81 is connected to a central power line 80 and which can be installed permanently at a dock in a marina for sensing corrosion currents which occur in any of the boats in the harbor. Transducer 81 generates on bus 82 a signal indicating the presence of a corrosion current which when connected through excitation circuit 84 and peak detector circuit 85 in a manner similar to that of the circuit illustrated in FIGS. 1-4 generates a signal on bus 86 which when coupled to logic circuit 87 provides an alarm signal on bus 88. Such an alarm signal could be connected to a conventional lamp or a remote display system 89 which would provide a visual indication to a harbor-master in a marina that a corrosion current or currents are being detected somewhere in the harbor and that precautionary measures should be enacted.

Test generator 91 provides via buses 93, 94 self testing capabilities for detector 79 and switch 92 is a magnetic switch for providing external changing of logic and control parameters to detector 79 to temporarily inhibit the latching effect of the alarm circuit. The embodiment illustrated in FIG. 10 is directed more to a permanent location as an alarm in a marina harbor while the embodiment illustrated in FIG. 1 is directed toward a portable unit for sensitive and specific analysis of conditions between a single boat and the rest of the harbor.

While a preferred embodiment has been shown and described in conjunction with a marina environment, it could be applied to other types of benign conductors such as hoses filled with water, welding power leads, and some telephone lines, since a transducer is passive in its interaction with the conductor(s) under test.

What is claimed is:

1. A maritime corrosion detector comprising:
   transducer means for detecting leakage electrical current in a conductor connected to one or more boats and for generating a first control signal representing the occurrence, level and polarized condition of said detected leakage current,
   means responsive to said first control signal for generating a second control signal representing whether said leakage current is AC or DC leakage current,
   means responsive to said first control signal for generating a third control signal corresponding to the polarized condition of said DC leakage current, and
   means responsive to said first, second and third control signals for generating a fourth control signal representing the corrosive activity of said detected leakage current.

2. A detector as in claim 1 further including digital display means for displaying the magnitude of said corrosion current.

3. A detector as in claim 2 further including means for detecting the magnitude of the resultant corrosion from said detected leakage current.

4. A detector as in claim 1 further including test means for testing said detector.

5. A detector as in claim 1 further including alarm means for generating an alarm signal when leakage current is detected in one or more of said boats.

6. A maritime corrosion detector comprising:
    transducer means for detecting leakage electrical current in a conductor connected to one or more boats and for generating a first control signal representing the polarized condition and level of said detected leakage current,
    means responsive to said first control signal for generating a second control signal representing whether said leakage current is AC or DC leakage current,
    means responsive to said first control signal for generating a third control signal corresponding to the polarized condition of said DC leakage current, and
    means responsive to said first, second and third control signals for generating a fourth control signal representing the corrosive activity of said detected leakage current.

7. A maritime corrosion current detector comprising:
    transducer means for detecting leakage electrical current in a conductor connected to one or more boats and for generating a first control signal representing the level and polarized condition of said detected leakage current,
    means for generating a second control signal representing whether said detected leakage current is AC or DC leakage current,
    means for generating a third control signal corresponding to the polarized condition of said DC leakage current, and
    means for generating a fourth control signal representing the rate of corrosive activity of said detected leakage current.

8. A maritime corrosion current detector comprising:
    transducer means for detecting AC or DC leakage electrical current in a conductor connected to one or more boats in a marina and for generating a first control signal representing the occurrence, level, and polarized condition of said detected leakage current,
    means responsive to said first control signal for generating a second control signal representing the rate of corrosive activity of said detected leakage current, and
    means responsive to said second control signal for generating an alarm signal thereby indicating the occurrence of said corrosive activity.

9. A maritime corrosion current detector comprising:
    transducer means for detecting AC or DC leakage electrical current in a conductor providing power to one or more boats and for generating a first control signal representing the occurrence, level and polarized condition of said leakage current,
    means responsive to said first control signal for generating a second control signal corresponding to the peak value of said first control signal, and
    means responsive to said first and second control signals for generating a third control signal corresponding to the magnitude of said first control signal thereby representing the corrosive activity of said detected leakage current.

10. A corrosion current detector comprising:
    transducer means for detecting leakage electrical current in a conductor and for generating a first control signal representing the magnitude and polarized condition of said leakage current,
    means for generating a second control signal representing whether said leakage current is AC or DC leakage current,
    means for generating a third control signal corresponding to the polarized condition of said DC leakage current, and
    means for generating a fourth control signal representing the corrosive activity of said detected leakage current.

* * * * *